(12) United States Patent
Sarkies

(10) Patent No.: US 12,226,426 B2
(45) Date of Patent: Feb. 18, 2025

(54) COMBINATION THERAPY

(71) Applicant: IMPERIAL COLLEGE INNOVATIONS LIMITED, London (GB)

(72) Inventor: Peter Sarkies, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 900 days.

(21) Appl. No.: 17/279,205

(22) PCT Filed: Sep. 25, 2019

(86) PCT No.: PCT/GB2019/052703
§ 371 (c)(1),
(2) Date: Mar. 24, 2021

(87) PCT Pub. No.: WO2020/065309
PCT Pub. Date: Apr. 2, 2020

(65) Prior Publication Data
US 2022/0031722 A1 Feb. 3, 2022

(30) Foreign Application Priority Data
Sep. 25, 2018 (GB) .................... 1815579

(51) Int. Cl.
*A61K 31/7036* (2006.01)
*A61K 31/255* (2006.01)

(52) U.S. Cl.
CPC ........ *A61K 31/7036* (2013.01); *A61K 31/255* (2013.01)

(58) Field of Classification Search
None
See application file for complete search history.

(56) References Cited

U.S. PATENT DOCUMENTS

2009/0264342 A1  10/2009  Cottarel et al.

FOREIGN PATENT DOCUMENTS

WO   WO-2006071685 A2 *  7/2006  ............. A61K 31/65

OTHER PUBLICATIONS

Guzel, C., et al., "In vitro Activities of Various Antibiotics, Alone and in Conmbination with Colistin Methanesulfonate, against Pseudomonas Aeruginosa Strains Isolated from Cystic Fibrosis Patients," Chemotherapy, vol. 54, pp. 147-151 (Mar. 6, 2008).
Jacobs, J. Y., et al., "Synergism between Gentamicin and Mitomycin C in Staphylococcal Infections in Mice," Chemotherapy, vol. 31, No. 5, pp. 389-394 (1985).
Humayun, M. Zafri, et al., Potential Roles for DNA Replication and Repair Functions in Cell Killing by Streptomycin, Mutation Research, vol. 749, No. 1-2, pp. 87-91 (Sep. 1, 2013).
Kang, T., et al., "The Aminoglycoside Antibiotic Kanamycin Damages DNA Bases in *Escherichia coli*: Caffeine Potentiates the DNA-Damaging Effects of Kanamycin while Suppressing Cell Killing by Ciprofloxacin in *Escherichia coli* and Bacillus Anthracis," Antimicrobial Agents and Chemotherapy, vol. 56, No. 6, pp. 3216-3223 (Jun. 2012).
Mielecki, D., et al., "Pseudomonas Putida AlkA and AlkB Proteins Comprise Different Defense Systems for the Repair of Alkylation Damage to DNA—In Vivo, In Vitro, and In Silico Studies," PLOS One, vol. 8(10):e76198, (Oct. 2, 2013).
Prasad, P.R., et al., "Mutagenic Activity of Antibiotics Alone and in Conjunction with Alkanesulfonates," Mutation Research, vol. 84, No. 1, pp. 83-90 (Nov. 1981).
Wild., D., "Chemical Induction of Streptomycin-Resistant Mutations in *Escherichia coli* Dose and Mutagenic Effects of Dichlorvos and Methyl Methanesulfonate," vol. 19, pp. 33-41 (1973).
International Search Report of PCT/GB2019/052703 dated Mar. 3, 2020.
Written Opinion of PCT/GB2019/052703 dated Mar. 3, 2020.
Great Britain Patent Office Search Report of Great Britain Patent Application No. 1815579.6 dated Apr. 4, 2019.
Cooper, B., et al., "Renal Dysfunction During High-Dose Cisplatin Therapy and Autologous Hematopoietic Stem Cell Transplantation: Effect of Aminoglycoside Therapy," The American Journal of Medicine, vol. 94, pp. 497-504 (May 1993).
Antimicrobial Agents and Chemotherapy, Apr. 1979, p. 580-586 vol. 15, Jacobs et al.

* cited by examiner

*Primary Examiner* — Traviss C McIntosh, III
(74) *Attorney, Agent, or Firm* — Much Shelist P.C.; Christopher M. Cabral

(57) ABSTRACT

The present invention provides a therapeutic combination for use in treating an infection with a pathogen. The therapeutic combination comprises an aminoglycoside antibiotic; and a nucleic acid monoalkylating agent that substitutes a single nucleotide of a nucleic acid with an alkyl group, wherein the therapeutic combination provides an enhanced suppression of a pathogen when compared with an otherwise identical composition lacking said aminoglycoside antibiotic; or wherein the therapeutic combination provides an enhanced suppression of a pathogen when compared with an otherwise identical composition lacking said nucleic acid monoalkylating agent; and kits for performing said method.

19 Claims, 2 Drawing Sheets

Specification includes a Sequence Listing.

SEQUENCE LISTING

<160> NUMBER OF SEQ ID NOS: 1

<210> SEQ ID NO 1
<211> LENGTH: 651
<212> TYPE: DNA
<213> ORGANISM: Escherichia coli

<400> SEQUENCE: 1

```
atgttggatc tgtttgccga tgctgaaccg tggcaagagc cactggcggc tggtgcggta      60
attttacggc gttttgcttt taacgctgcg gagcaactga tccgcgatat taatgacgtt     120
gccagccagt cgccgtttcg ccagatggtc accccggg gatataccat gtcggtggcg      180
atgaccaact gtgggcatct gggctggacg acccatcggc aaggttatct ctattcgccc     240
attgatccgc aaacaaataa accgtggccc gccatgccac agagttttca taatttatgt     300
caacgtgcgg ctacggcggc gggctatcca gatttccagc cagatgcttg tcttatcaac     360
cgctacgctc ctggcgcgaa actgtcgctg catcaggata aagacgaacc ggatctgcgc     420
gcgccaattg tttctgtttc tctgggctta cccgcgattt ttcaatttgg cggcctgaaa     480
cgaaatgatc cgctcaaacg tttgttgttg aacatggcg atgtggtggt atggggcggt     540
gaatcgcggc tgttttatca cggtattcaa ccgttgaaag cggggtttca tccactcacc     600
atcgactgcc gctacaacct gacattccgt caggcaggta aaaagaata a               651
```

COMBINATION THERAPY

The present invention relates to a combination therapy of an antibiotic and an alkylating agent, and uses thereof as a medicament and for the control of pathogens.

Alkylation of DNA is an important regulatory mechanism in eukaryotes, with important functions such as transposable element (TE) silencing and gene regulation. Notably, DNA methylation at the 5 position of cytosine (5-methylcytosine, 5meC) is a key epigenetic mark in eukaryotes, which can be maintained through DNA replication by way of DNA methyltransferase (DNMT) activity.

Chemotherapy has exploited the fact certain DNA alkylation events are toxic (such as 3-methylcytosine, 3meC), and as such has used alkylating agents to induce the introduction DNA damage leading to cytotoxicity of cancer cells. Such chemotherapy has mainly focused on the use of alkylating antineoplastic agents which typically result in the substitution of guanine with an alkyl group, e.g. at the number 7 nitrogen atom of the purine ring.

However, such alkylating agents have not found routine utility as antimicrobials, mainly due to the hazardous nature of typical alkylating agents which has confined their use to defined therapies (e.g. cancer therapy). To our knowledge, there has been no reported use of an alkylating agent as a routine treatment for infections (e.g. bacterial infections), and particularly which does not require a dosage which also results in the side effects of alkylating agents seen in chemotherapy. Demonstrating this, the present inventors have found that the growth of wildtype bacteria is not suppressed in the presence of an alkylating agent (see Example 1). The latter may be exacerbated by the presence of enzymes in cells (e.g. bacterial cells) which control/reverse toxic DNA alkylation, leading to lower efficacy at doses of alkylating agent which can be perturbed by such enzymes. Indeed, toxic 3-methylcytosine (3meC) alkylation is reversed by AlkB (and its homologues), and the present inventors have recently found that this mechanism appears to have evolved together with DNA methyltransferase activity which surprising results in 'off-target' 3meC alkylation (controlled by AlkB) as well as 5meC alkylation.

There therefore exists a need for means and methods which enhance the cytotoxic effects of compositions having and alkylating agent, and which allows for their practical utility in therapy beyond chemotherapy.

The present invention addresses one or more of the above mentioned problems.

The present invention is predicated on the surprising finding that an antibiotic (e.g. an aminoglycoside antibiotic) can be used to work in synergy with a monofunctional alkylating agent (e.g. monoalkyating agent) to provide a toxic combination, increasing cellular cytotoxicity following contact with a combination of these agents. Thus, a seminal finding of the present invention is that a combination therapy can be employed to target pathogenic infections, pathogens in general, as well as increasing the efficacy of currently existing chemotherapeutics.

In one aspect the invention provides a therapeutic combination for use in treating an infection with by a pathogen, said therapeutic combination comprising:
    a. an antibiotic; and
    b. a nucleic acid monoalkylating agent that substitutes a single nucleotide of a nucleic acid with an alkyl group (e.g. methyl group).

Another aspect of the invention provides a method of treating a subject having an infection with a pathogen, the method comprising administering the therapeutic combination to the subject, wherein said therapeutic combination comprises:
    a. an antibiotic (preferably an aminoglycoside antibiotic); and
    b. a nucleic acid monoalkylating agent that substitutes a single nucleotide of a nucleic acid with an alkyl group (e.g. methyl group).

In another aspect, there is provided a therapeutic combination (e.g. composition) comprising:
    a. an antibiotic (preferably an aminoglycoside); and
    b. a nucleic acid monoalkylating agent that substitutes a single nucleotide of a nucleic acid with an alkyl group.

In one embodiment, said antibiotic is one or more selected from an aminoglycoside antibiotic, a penicillin antibiotic, a cephalosporin antibiotic, a macrolide antibiotic, a fluoroquinolone antibiotic, a sulphonamide antibiotic, and a tetracycline antibiotic, or a combination thereof. In one embodiment, said antibiotic is one or more selected from an aminoglycoside antibiotic, a penicillin antibiotic, a cephalosporin antibiotic, a macrolide antibiotic, a fluoroquinolone antibiotic, a sulphonamide antibiotic, or a combination thereof.

In a preferable embodiment, said antibiotic is an aminoglycoside antibiotic.

In one aspect the invention provides a therapeutic combination for use in treating an infection with by a pathogen, said therapeutic combination comprising:
    a. an aminoglycoside antibiotic; and
    b. a nucleic acid monoalkylating agent that substitutes a single nucleotide of a nucleic acid with an alkyl group.

In another aspect, there is provided a therapeutic combination (e.g. composition) comprising:
    a. an aminoglycoside antibiotic; and
    b. a nucleic acid monoalkylating agent that substitutes a single nucleotide of a nucleic acid with an alkyl group.

The following embodiments and definitions may pertain to any aspect or embodiment of the invention described herein e.g. to any aspect or embodiment of any method, use, composition, therapeutic combination, therapeutic combination for use, agent combination for use, kit, or kit for use described herein.

In one embodiment, the therapeutic combination provides an enhanced suppression of a pathogen when compared with an otherwise identical composition lacking said antibiotic (preferably wherein the antibiotic is an aminoglycoside antibiotic). In one embodiment, the therapeutic combination provides an enhanced suppression of a pathogen when compared with an otherwise identical composition lacking said nucleic acid monoalkylating agent (that substitutes a single nucleotide of a nucleic acid with an alkyl group).

In one embodiment, the therapeutic combination provides an enhanced suppression of an infection with a pathogen when compared with an otherwise identical composition lacking said antibiotic (preferably wherein the antibiotic is an aminoglycoside antibiotic). In one embodiment, the therapeutic combination provides an enhanced suppression of an infection with a pathogen when compared with an otherwise identical composition lacking said nucleic acid monoalkylating agent (that substitutes a single nucleotide of a nucleic acid with an alkyl group).

The term "infection with a pathogen" may be used synonymously with the term "infection caused by a pathogen".

The term "nucleic acid monoalkylating agent" is used synonymously with the term "monofunctional alkylating agent" herein. Said terms refer to an agent that substitutes a nucleic acid (or, more particularly, a nucleotide of said nucleic acid) with an alkyl group, such as a methyl group. Preferably, a nucleic acid monoalkylating agent (e.g. monofunctional alkylating agent) substitutes a single nucleotide with a single alkyl group (e.g. methyl group).

A "nucleic monoalkylating agent" as described herein is a nucleic monoalkylating agent that substitutes a single nucleotide of a nucleic acid with an alkyl group The nucleotide alkylation caused by such monoalkylating agents represents a form of DNA damage that may be permanent, such that said agents cause cytotoxicity. The monoalkylating agents represent one broad class of nucleic acid alkylating agents, with another class being the "bifunctional alkylating agents". A bifunctional alkylating agent typically substitutes at least two nucleotides with an alkyl group.

Bifunctional alkylating agents are both structurally and functionally distinct from monofunctional alkylating agents. For example, while a monoalkylating agent typically has a single alkyl group for substituting a nucleotide (with said alkyl group), a bifunctional alkylating agent typically has at least two such alkyl groups for substituting a nucleotide. Furthermore, upon contacting DNA, bifunctional alkylating agents typically cause intrastrand and/or interstrand cross-linking, which is understood to be due to an interaction between two different alkyl substituents present on two different nucleotides (e.g. on two different strands).

The different types of DNA damage caused by such alkylating agents also require different modes of DNA repair (e.g. different DNA repair pathways) for the removal or tolerance of said damage. For example, a single alkylated nucleotide (monoalkylating agent), such as 3meC, may be removed (e.g. by base excision repair) or repaired (e.g. via AlkB-catalysed removal of the alkyl group), allowing for cell survival. In contrast, interstrand cross-link repair mechanisms are complex, and are understood to represent a formidable block to the DNA replication machinery. For example, there may be a requirement for a combination of FA repair, NER, translesion synthesis (TLS), and HR repair for efficient repair of cross-linked DNA (caused by bifunctional alkylating agents).

As such, a monoalkylating agent may advantageously be less toxic (relative to a bifunctional alkylating agent) to a subject to which a therapeutic combination of the invention is employed, as cells of the subject are typically better equipped to remove/repair the resulting DNA damage, whereas the target cells (e.g. pathogens) may be less well equipped to remove/repair such resulting DNA damage (for example, where the pathogen lacks an a/kb homologue). As such, the effect of the therapeutic combination may be specific to a pathogen (e.g. bacterium), and cause less 'off-target' effects to cells of the (infected) subject (relative to an otherwise identical combination comprising a bifunctional alkylating agent instead of a monoalkylating agent).

In one embodiment, a nucleic acid monoalkylating agent comprises a single alkyl group (e.g. a single reactive alkyl group).

In one embodiment, a nucleic acid monoalkylating agent described herein does not cause a DNA intrastrand and/or interstrand cross-link (e.g. upon contacting DNA).

In one embodiment, a nucleic acid monoalkylating agent described herein is an $S_N1$ and/or $S_N2$ type agent. For example, the nucleic acid monoalkylating agent may be an $S_N1$ type agent. Alternatively (or additionally), the nucleic acid monoalkylating agent may be an $S_N2$ type agent.

The term "treating" may mean that an infection is treated (e.g. the infection is removed), suppressed, or reduced, or that the symptoms of an infection are reduced. Preferably, said treating is used to provide a clinical end-point in which a subject to which a therapeutic combination of the invention is administered has a reduced level of infection than immediately prior to administration of the therapeutic combination.

The term "treat" or "treating" as used herein encompasses prophylactic treatment (e.g. to prevent onset of a disease) as well as corrective treatment (treatment of a subject already suffering from a disease). Preferably "treat" or "treating" as used herein means corrective treatment. The term "treat" or "treating" encompasses treating both the disease and/or infection and a symptom thereof. In some embodiments "treat" or "treating" refers to a symptom of a disease and/or infection.

Therefore, a therapeutic combination of the invention may be administered to a subject in a therapeutically effective amount or a prophylactically effective amount.

A "therapeutically effective amount" is any amount of the therapeutic combination, which when administered alone or in combination to a subject for treating a disease and/or infection (or a symptom thereof) is sufficient to effect such treatment of the disease and/or infection, or symptom thereof.

A "prophylactically effective amount" is any amount of the therapeutic combination that, when administered alone or in combination to a subject inhibits or delays the onset or reoccurrence of a disease and/or infection (or a symptom thereof). In some embodiments, the prophylactically effective amount prevents the onset or reoccurrence of a disease and/or infection entirely. "Inhibiting" the onset means either lessening the likelihood of disease and/or infection onset (or symptom thereof), or preventing the onset entirely.

Without wishing to be bound by theory, it is believed that an antibiotic (aminoglycoside antibiotic) enhances the activity of a a nucleic acid monoalkylating agent, or vice versa. Thus, a cell or a pathogen (e.g. a bacterium) treated with a combination of these agents (e.g. drugs) suffers an increased level of nucleic acid (e.g. nucleotide) alkylation (causing e.g. 3meC) compared to a cell or pathogen treated with a monoalkylating agent alone, and the cell or pathogen's growth is subsequently suppressed due to toxic nucleic acid damage. Thus, antibiotic (e.g. aminoglycoside antibiotic) treatment may sensitise a cell/pathogen to a monoalkylating agent, improving the efficacy thereof (or vice versa). This synergy is not limited to bacterial cells which are sensitive to an aminoglycoside antibiotic (e.g. via a conical mechanism), and indeed has been observed in bacterial cells having resistance (e.g. comprising a resistance-conferring gene) to the exemplary aminoglycoside antibiotic tested (see Example 1).

Thus, in one aspect there is provided use of an antibiotic for enhancing the alkylation of a nucleic acid (e.g. of a nucleotide of said nucleic acid) by a nucleic acid monoalkylating agent that substitutes a single nucleotide with an alkyl group. Said nucleic acid may be RNA or DNA (preferably DNA).

In one aspect there is provided use of an aminoglycoside antibiotic for enhancing the alkylation of a nucleic acid (e.g. of a nucleotide of said nucleic acid) by a further nucleic acid monoalkylating agent. Said nucleic acid may be RNA or DNA (preferably DNA).

This newly discovered utility of an antibiotic (e.g. aminoglycoside antibiotic) to enhance (e.g. synergistically enhance) the activity of a nucleic acid monoalkylating agent is particularly surprising as, for example, aminoglycoside antibiotics have hitherto been employed principally as disruptors of ribosomal-activity (which is a mechanistically distinct way of inducing cytotoxicity). Thus, not only have the inventors identified a new technical field of application (i.e. beyond the field of traditional antibiotic therapy), they have also identified an unexpected technical effect with said field (i.e. enhanced activity of a nucleic acid monoalkylating agent).

Advantageously, this combination therapy (therapeutic combination for use) provides purposeful use of such antibiotics for targeting cells/organisms that would normally be unreactive (unresponsive) to such antibiotics (e.g. non-bacterial cells/organisms, or antibiotic-resistant bacteria). Furthermore, due to the synergistic nature of the combination, lower doses of the antibiotics and alkylating agents may be employed, thus reducing the risk of the development of antibiotic resistance (a fundamental public health threat) due to overuse. Indeed, the present invention reduces the need for the prescription of chronic antibiotic regimens, for example to immunocompromised subjects.

As many antibiotics are relatively inexpensive, the enhanced therapeutic combination of the present invention represents a significant cost saving solution for public health agencies and patients due to the decreased amount of typically more expensive monoalkylating agents required for therapy.

Furthermore, the present invention allows the derivation of clinical use from antibiotics which are rarely used due to toxicity at traditional doses. Indeed, the therapeutic combination (by lowering the necessary therapeutic dose) renders such antibiotics of broader application.

The order of application/administration of the component parts of the combination therapy can be varied. The antibiotic (e.g. aminoglycoside antibiotic) and the nucleic acid monoalkylating agent can be administered simultaneously (e.g. both at their own particular optimal dose for achieving synergy), either as part of a single composition or within separate compositions. For example, the monoalkylating agent may be present in a first composition (e.g. for intravenous administration to a subject) and the antibiotic may be present in a second composition (e.g. for oral administration to a subject).

Furthermore, the antibiotic (preferably an aminoglycoside antibiotic) and the nucleic acid monoalkylating agent may be administered at different times (e.g. an aminoglycoside antibiotic may be pre-administered to sensitise a cell to the alkylating agent). Thus, in a further embodiment an aminoglycoside antibiotic and a nucleic acid monoalkylating agent are administered to a subject at different times, within separate compositions.

In one embodiment an antibiotic (preferably an aminoglycoside antibiotic) is administered prior to a nucleic acid monoalkylating agent. In one embodiment an antibiotic is administered simultaneously with a nucleic acid monoalkylating agent. In one embodiment an antibiotic is administered sequentially to a monoalkylating agent.

In one embodiment an aminoglycoside antibiotic is administered prior to a nucleic acid monoalkylating agent. In one embodiment an aminoglycoside antibiotic is administered simultaneously with a nucleic acid monoalkylating agent. In one embodiment an aminoglycoside antibiotic is administered sequentially to a nucleic acid monoalkylating agent.

Suitably, the therapeutic combination is administered to a subject. The terms "subject", "individual" and "patient" are used interchangeably herein to refer to a mammalian subject. In one embodiment the "subject" is a human, a companion animal (e.g. a pet such as a dog, cat, and/or rabbit), livestock (e.g. a pig, sheep, cattle, and/or a goat), and/or a horse. In a preferable embodiment, the subject is a human.

In one embodiment, an infection is an acute infection. In one embodiment, and infection is a chronic infection.

In methods of the invention, the subject may not have been previously diagnosed as having an infection. Alternatively, the subject may have been previously diagnosed as having an infection. The subject may also be one who exhibits disease risk factors, or one who is asymptomatic for an infection. The subject may also be one who is suffering from or is at risk of developing an infection. In one embodiment, the subject has been previously administered a therapy for an infection.

Advantageously, given the synergistic nature of the present therapeutic combination, a minimal dose of an antibiotic may be administered, which allows for greater flexibility in the use of antibiotics (e.g. aminoglycoside antibiotics) which have traditionally only been prescribed for particular uses and/or administration.

Suitably, a dose of the therapeutic combination may be chosen which balances the efficacy of the therapeutic combination for suppressing an infection against damage to non-infected cells of the host (e.g. the healthy cells of an infected subject). Preferably, a dose of the therapeutic combination which is not toxic to a human subject (e.g. to a human cell) may be used. This is particularly advantageous as some antibiotics may cause side effects at high doses—for example, certain aminoglycoside antibiotics (e.g. kanamycin) cause ototoxicity at high doses. Thus, a therapeutic combination of the present invention may be used to prevent the risk of the development of ototoxicity.

Exemplifying the broadened utility of antibiotics (e.g. aminoglycoside antibiotics) and nucleic acid monoalkylating agents when employed as a synergistic combination, the present invention encompasses a combination of an antibiotic (e.g. aminoglycoside antibiotic) and a nucleic acid monoalkylating agent for general use to suppress a pathogen, for example as a disinfectant. Synergism between the component parts means that a relatively dilute composition/solution (or any other formulation) comprising relatively low concentrations of an antibiotic and a nucleic acid monoalkylating agent (or alkylating-like agent) may be applied to a pathogen, yet achieve similar (or even greater) levels of suppression that would otherwise only be possible with a much higher concentration of the individual component parts.

In one aspect, there is provided use of an agent combination as a disinfectant (preferably an in vitro disinfectant), wherein said agent combination (e.g. disinfectant) comprises:
a. an antibiotic; and
b. a nucleic acid monoalkylating agent that substitutes a single nucleotide of a nucleic acid with an alkyl group.

In one aspect, there is provided use of an agent combination as a disinfectant, wherein said agent combination (e.g. disinfectant) comprises:
a. an aminoglycoside antibiotic; and
b. an nucleic acid monoalkylating agent that substitutes a single nucleotide of a nucleic acid with an alkyl group.

In one embodiment, the agent combination provides an enhanced suppression of a pathogen when compared with an otherwise identical composition lacking said aminoglycoside antibiotic. Additionally or alternatively, the agent combination may provide an enhanced suppression of a pathogen when compared with an otherwise identical composition lacking said nucleic acid monoalkylating agent.

Suitably, said use may comprise applying said disinfectant (e.g. therapeutic combination) at a site comprising a pathogen, a site suspected of comprising a pathogen, or at a site at risk of comprising a pathogen.

The term "disinfectant" refers to a formulation (e.g. composition or solution) which suppresses a pathogen. Such use as a disinfectant is not limited to use to destroy the cell wall of a pathogen (e.g. a microbe) or use to infer with the metabolism of a pathogen. Indeed, the present invention provides advantageous means of disinfection by causing toxic alkylation damage to a nucleic acid of a pathogen, thus broadening the array of disinfectant solutions available.

The term "suppresses" or "suppressing" may mean "inhibiting the growth of" or "killing" a pathogen (or other target cell). The term "inhibits" or "inhibiting" are synonymous with the term "retards the growth of" a pathogen (or other target cell/organism). In one embodiment, a therapeutic combination of the invention may "kill" a pathogen (or other target cell/organism) or be "used to kill" a pathogen (or other target cell/organism). The term "suppressing" also encompasses preventing the growth of a pathogen (or other target cell/organism) e.g. when applied as a pre-treatment to prevent contamination with a pathogen (or other target cell/organism).

In a further aspect, there is provided an in vitro method of suppressing the growth of a pathogen, said method comprising applying a disinfectant comprising a combination of an antibiotic and a nucleic acid monoalkylating agent (that substitutes a single nucleotide of a nucleic acid with an alkyl group) to a site, wherein said site is:
  i. a site comprising a pathogen;
  ii. a site suspected of comprising pathogen; or
  iii. a site at risk of comprising a pathogen.

In a further aspect, there is provided an in vitro method of suppressing the growth of a pathogen, said method comprising applying a disinfectant comprising a combination of an aminoglycoside antibiotic and a nucleic acid monoalkylating agent (that substitutes a single nucleotide with an alkyl group) to a site, wherein said site is:
  i. a site comprising a pathogen;
  ii. a site suspected of comprising pathogen; or
  iii. a site at risk of comprising a pathogen.

In one embodiment, an agent combination and/or disinfectant of the invention may be applied or used at one or more site selected from medical equipment, bedding, furniture, walls, or floors such as or floors in a hospital, or a combination thereof.

Suitable medical equipment may be one or more selected from a grasper, clamp and/or occluder (e.g. for blood vessels and other organs), needle driver (e.g. for holding suture needles), retractor (e.g. for spreading skin), mechanical cutter (e.g. scalpel, lancet, drill bit, rasp, trocars, Ligasure, Harmonic scalpel, surgical scissors, rongeur etc.), injection needle, intubator, or a combination thereof.

In one embodiment, a use or method of the invention comprises providing a local concentration of an antibiotic (preferably an aminoglycoside antibiotic) and a nucleic acid monoalkylating agent at a site of about 1 mM to about 200 mM (e.g. about 20 mM-180 mM, about 40 mM-160 mM, about 60 mM-140 mM, or about 80 mM-120 mM).

Suitably, there may be provided a local concentration of an antibiotic (preferably an aminoglycoside antibiotic) at a site of about 80 mM to about 120 mM (e.g. about 85 mM-115 mM, about 90 mM-110 mM, or about 95 mM-100 mM). In one embodiment, a local concentration of a nucleic acid monoalkylating agent may be provided at a site of about 1 mM to about 40 mM (e.g. about 5 mM-35 mM, 10 mM-30 mM, or 15 mM-25 mM).

In a preferable embodiment, there may be provided a local concentration of an antibiotic (preferably an aminoglycoside antibiotic) at a site of about 80 mM to about 120 mM (e.g. about 85 mM-115 mM, about 90 mM-110 mM, or about 95 mM-100 mM) and a local concentration of an alkylating agent at a site of about 1 mM to about 40 mM (e.g. about 5 mM-35 mM, 10 mM-30 mM, or 15 mM-25 mM).

In one aspect, there is provided use of a nucleic acid monoalkylating agent for enhancing the suppression of a pathogen by of an antibiotic (preferably an aminoglycoside antibiotic), wherein said nucleic acid monoalkylating agent is a nucleic acid monoalkylating agent that substitutes a single nucleotide of a nucleic acid with an alkyl group.

In one aspect, there is provided use of an antibiotic (preferably an aminoglycoside antibiotic) for enhancing the suppression of a pathogen by a nucleic acid monoalkylating agent, wherein said nucleic acid monoalkylating agent is a nucleic acid monoalkylating agent that substitutes a single nucleotide of a nucleic acid with an alkyl group.

In one aspect, there is provided use of a nucleic acid monoalkylating agent for enhancing the bactericidal activity of an antibiotic, wherein said nucleic acid monoalkylating agent is a nucleic acid monoalkylating agent that substitutes a single nucleotide of a nucleic acid with an alkyl group.

In one aspect, there is provided use of a nucleic acid monoalkylating agent for enhancing the bactericidal activity of an aminoglycoside antibiotic, wherein said nucleic acid monoalkylating agent is a nucleic acid monoalkylating agent that substitutes a single nucleotide of a nucleic acid with an alkyl group.

In another aspect, there is provided use of an antibiotic for promoting (e.g. enhancing) the introduction of alkylation damage (e.g. 3meC) to a nucleic acid by a nucleic acid monoalkylating agent, wherein said nucleic acid monoalkylating agent substitutes a single nucleotide of a nucleic acid with an alkyl group.

In another aspect, there is provided use of an aminoglycoside antibiotic for promoting (e.g. enhancing) the introduction of alkylation damage (e.g. 3meC) to a nucleic acid by a nucleic acid monoalkylating agent, wherein said nucleic acid monoalkylating agent substitutes a single nucleotide with an alkyl group.

A therapeutic combination or disinfectant of the invention may suitably be provided as part of a kit, which may for example be labelled or include an instruction manual outlining a suitable use (or uses) of the kit.

In one aspect, there is provided a kit comprising:
  a. an antibiotic; and
  b. a nucleic acid monoalkylating agent that substitutes a single nucleotide of a nucleic acid with an alkyl group.

In one aspect, there is provided a kit comprising:
  a. an aminoglycoside antibiotic; and
  b. a nucleic acid monoalkylating agent that substitutes a single nucleotide of a nucleic acid with an alkyl group.

Said kit may further comprise a housing for containing the antibiotic (preferably aminoglycoside antibiotic) and the nucleic acid monoalkylating agent.

In one aspect, said kit may be for use in treating an infection caused by a pathogen. In another aspect, said kit may be for use as a disinfectant. In a yet further aspect, said kit may be used in an in vitro method for suppressing a pathogen.

In one embodiment, an aminoglycoside antibiotic and a nucleic acid monoalkylating agent are comprised within the same composition. In another embodiment, an aminoglycoside antibiotic and a nucleic acid monoalkylating agent are comprised within separate compositions.

In one embodiment, a kit may comprise instructions to use the kit in a method for treating an infection with a pathogen. Said instructions may include, for example, the optimal dose of a therapeutic combination to be administered, the optimal time(s) to administer a therapeutic combination, the optimal administration method(s), or any other information relevant to using a therapeutic combination of the invention to treat a pathogenic infection (e.g. to treat an infectious disease).

Said instructions may be provided as part of a label, or as part of an instruction manual provided either together with or separately to the kit.

In one embodiment, a kit may comprise instructions to use the kit as a disinfectant. Said instructions may include, for example, the optimal concentration of a therapeutic combination to be applied as a disinfectant, the optimal time(s) to apply the disinfectant, the optimal application method(s), or any other information relevant to using a therapeutic combination of the invention as a disinfectant.

In one embodiment, a kit may comprise instructions to use the kit in an in vitro method for suppressing a pathogen.

A kit provided as a disinfectant or for use in an in vitro method for suppressing a pathogen may suitably be a ready to use (RTU) kit. Thus, in one embodiment a kit may be a RTU kit for use as a disinfectant or for use in an in vitro method for suppressing a pathogen. A disinfectant (e.g. comprising an aminoglycoside antibiotic and a nucleic acid monoalkylating agent) may be applied by spraying, pouring, swabbing, or rubbing said disinfectant at a site of interest.

A therapeutic combination of the infection may also be provided on material for protecting or suturing a wound. For example, a therapeutic combination of the invention may be provided on a wound dressing (e.g. bandage and/or plaster), a gauge, a suture or a combination thereof.

Since nucleic acid alkylation damage may result in toxicity in a multitude of organisms/microorganisms, the present invention surprisingly allows use of an aminoglycoside antibiotic in organisms beyond bacteria.

Thus, in one embodiment a pathogen may be one or more selected from a bacterium, a virus, a protist, a fungus, a helminth, or a combination thereof.

In one embodiment a pathogen may be one or more selected from a bacterium, a protist, a fungus, a helminth, or a combination thereof.

In a preferable embodiment, said pathogen is a bacterium.

Said bacterium may be one or more selected from a *Salmonella* spp, a *Pseudomonas* spp, a *Mycobacterium* spp, an *Escherichia* spp, a *Proteus* spp, a *Serratia* spp, a *Klebsiella* spp, an *Acinetobacter* spp or a combination thereof.

Preferably, said pathogen is one or more selected from a *Salmonella* spp, a *Pseudomonas* spp, a *Mycobacterium* spp or a combination thereof.

Said *Salmonella* spp may be one or more selected from *S. bongori*, *S. enterica*, or a combination thereof. Suitably, said *Salmonella* spp may be *S. enterica* (e.g. *S. enterica* serovar Typhimurium).

Said *Pseudomonas* spp may be one or more selected from *P. aeruginosa*, *P. alcaligenes*, *P. anguilliseptica*, *P. argentinensis*, *P. borbori*, *P. citronellolis*, *P. flavescens*, *P. mendocina*, *P. nitroreducens*, *P. oleovorans*, *P. pseudoalcaligenes*, *P. resinovorans*, *P. straminea*, or a combination thereof. Suitably, said *Pseudomonas* may be *P. aeruginosa* (e.g. *P. aeruginosa* PAO1).

Said *Mycobacterium* spp may be one or more selected from *M. africanum*, *M. bovis*, *M. bovis* BCG, *M. canetti*, *M. caprae*, *M. microti*, *M. mungi*, *M. orygis*, *M. pinnipedii*, *M. suricattae*, *M. tuberculosis*. Suitably, said *Mycobacterium* may be *M. tuberculosis*.

Said *Escherichia* spp may be one or more selected from *E. albertii*, *E. coli*, *E. fergusonii*, *E. hermannii*, *E. marmotae*, *E. vulneris* or a combination thereof. Suitably, said *Escherichia* spp may be *E. coli*.

Said *Proteus* spp may be one or more selected from *P. hauseri*, *P. mirabilis*, *P. myxofaciens*, *P. penneri*, *P. vulgaris*, or a combination. Suitably, said *Proteus* spp may be *P. vulgaris*.

Said *Serratia* spp may be *S. marcescens*.

Said *Klebsiella* spp may be one or more selected from *K. aerogenes*, *K. granulomatis*, *K. oxytoca*, *K. michiganensis*, *K. pneumoniae*, *K. quasipneumoniae*, *K. grimontii*, *K. variicola*, or a combination thereof. Suitably, said *Klebsiella* spp. may be *K. pneumoniae*.

Said *Acinetobacter* spp may be one or more selected from *A. albensis*, *A. apis*, *A. baumannii*, *A. beijerinckii*, *A. bereziniae*, *A. bohemicus*, *A. boissieri*, *A. bouvetii*, *A. brisouii*, *A. calcoaceticus*, *A. celticus*, *A. colistiniresistens*, *A. courvalinii*, *A. defluvii*, *A. disperses*, *A. dijkshoorniae*, *A. equi*, *A. gandensis*, *A. gemeri*, *A. guangdongensis*, *A. guillouiae*, *A. gyllenbergii*, *A. haemolyticus*, *A. harbinensis*, *A. indicus*, *A. junii*, *A. kookii*, *A. lactucae*, *A. larvae*, *A. lwoffii*, *A. modestus*, *A. nectaris*, *A. nosocomialis*, *A. parvus*, *A. pakistanensis*, *A. populi*, *A. proteolyticus*, *A. pittii*, *A. piscicola*, *A. pragensis*, *A. proteolyticus*, *A. puyangensis*, *A. qingfengensis*, *A. radioresistens*, *A. rudis*, *A. schindleri*, *A. seifertii*, *A. soli*, *A. tandoii*, *A. tjernbergiae*, *A. towneri*, *A. ursingii*, *A. variabilis*, *A. venetianus*, *A. vivianii*, or a combination thereof. Suitably, said *Acinetobacter* spp may be *A. baumannii*.

In one embodiment, the pathogen is a fungi. Suitably, said fungi is a *Candida* spp.

Said *Candida* spp. may be one or more selected from *C. albicans*, *C. ascalaphidarum*, *C. amphixiae*, *C. Antarctica*, *C. argentea*, *C. atlantica*, *C. atmosphaerica*, *C. auris*, *C. blattae*, *C. bromeliacearum*, *C. carpophila*, *C. carvajalis*, *C. cerambycidarum*, *C. chauliodes*, *C. corydalis*, *C. dosseyi*, *C. dubliniensis*, *C. ergatensis*, *C. fructus*, *C. glabrata*, *C. fermentati*, *C. guilliermondii*, *C. haemulonii*, *C. humilis*, *C. insectamens*, *C. insectorum*, *C. intermedia*, *C. jeffresii*, *C. kefyr*, *C. keroseneae*, *C. krusei*, *C. lusitaniae*, *C. lyxosophila*, *C. maltose*, *C. marina*, *C. membranifaciens*, *C. mogii*, *C. oleophila*, *C. oregonensis*, *C. parapsilosis*, *C. quercitrusa*, *C. rugose*, *C. sake*, *C. shehatea*, *C. temnochilae*, *C. tenuis*, *C. these*, *C. tolerans*, *C. tropicalis*, *C. tsuchiyae*, *C. sinolaborantium*, *C. sojae*, *C. subhashii*, *C. viswanathii*, *C. utifis*, *C. ubatubensis*, and *C. zemplinina*. Suitably, Said *Candida* spp. may be *C. albicans*.

In another embodiment, said pathogen is a helminth. Said helminth may be one or more selected from the phyla Annelida, Platyhelminthes, Nematoda and Acanthocephala.

In one embodiment, said helminth is a parasitic flatworm. Said parasitic flatworm may be one or more selected from a Cestoda, a Trematoda and a Monogenea.

In one embodiment, said helminth is a parasitic nematode. Said parasitic nematode may be one or more selected an ascarid (*Ascaris*), a filaria, a hookworm, a pinworm (*Enterobius*), and a whipworm (*Trichuris trichiura*).

In a preferable embodiment, pathogen lacks one or more gene encoding a polypeptide that removes an alkyl group from an alkylated nucleotide adduct. For example, a pathogen may lack an alka or a/kb gene encoding a polypeptide that removes an alkyl group from an alkylated nucleotide adduct. In a preferable embodiment, a pathogen may lack an a/kb gene encoding a polypeptide that removes an alkyl group from an alkylated nucleotide adduct.

Reference to a pathogen or cell that lacks one or more gene as described herein embraces a pathogen or cell that comprises a mutant form of said gene that encodes a non-functional polypeptide (or polypeptide having reduced function).

In one embodiment, said alkylated nucleotide adduct is one or more selected from 3meC, 3meG, 3meA, 8-oxo-G, O2-alkylthymine, O4-alkylthymine, O6-methylguanine, and O6-ethylguanine. In one embodiment, said alkylated nucleotide adduct is one or more selected from 3meC, 3meG, 3meA, O2-alkylthymine, O4-alkylthymine, O6-methylguanine, and O6-ethylguanine.

AlkB protein is a protein involved in the direct reversal of alkylation damage (which, as the present inventors have elucidated, includes the reversal of 3meC). The A/kB gene was originally discovered in *E. coli*. A gene having high sequence identity and or expressing a protein having the same or similar function to the *E. coli* A/kB gene is referred to as an "AlkB homologue". Thus, the term a/kB as used herein embraces an a/kB homologue. Thus reference to pathogen or cell that lacks an a/kb embraces a pathogen or cell that lacks a homologue thereof (an a/kb homologue). Likewise, reference to pathogen or cell that lacks an alkb embraces a cell that lacks a homologue thereof (an alkb homologue).

The term alka also embraces an alka homologue.

In one embodiment, a pathogen may lack one or more gene encoding a polypeptide that promotes tolerance of a cell to the presence of an alkylated nucleotide adduct within a nucleic acid of the cell. For example, a pathogen may an Ada, OGT, RecA, DinB, and/or UmuCD gene encoding a polypeptide that promotes tolerance of a cell to the presence of an alkylated nucleotide adduct within a nucleic acid of the cell.

Ada and OGT are enzymes that repair 8-Oxoguanine (8-oxo-G), which results from alkylating damage of guanine; AlkA repairs 3-methylguanine (3meG) and 3-methyladenine (3meA); RecA promotes tolerance of DNA damage; and DinB and UmuCD (translesion DNA polymerases) allows cells to bypass alkylation damage.

The terms Ada, OGT, RecA, DinB, and UmuCD as used herein embraces an Ada, OGT, RecA, DinB, and UmuCD homologue, respectively.

The *Escherichia coli* AlkB protein is an iron- and 2-oxoglutarate-dependent oxygenase, principally responsible for repairing 1-methyladenine and 3-methylcytosine lesions in DNA (e.g. be removing alkyl-groups from nucleic acid, as shown in FIG. 2). AlkB homologues are also present in a number of prokaryotic and eukaryotic species. For example, nine human homologs of AlkB are known to exist, namely Alkb homolog 1 (NCBI Gene ID: 8846), histone h2a dioxygenase, ALKBH2 (GeneID: 121642), ALKBH3 (GeneID: 221120), ALKBH4 (NCBI GeneID: 54784), ALKBH5 (NCBI GeneID: 54890), ALKBH6 (NCBI GeneID: 84964), ALKBH7 (NCBI GeneID: 84266), ALKBH8 (NCBI GeneID: 91801), and FTO (NCBI GeneID: 79068).

A DNMT (DNA methyltransferase) is an enzyme that catalyses the alkylation (e.g. methylation) of a nucleic acid (e.g. at CpG sites on DNA).

For example, a nucleotide of a nucleic acid may be alkylated to provide a nucleotide adduct, such as 5meC and/or 3meC:

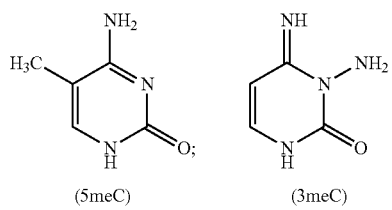

(5meC)　　　(3meC)

The present inventors have recently found that organisms in which DNA is found to be methylated (e.g. as part of epigenetic control of gene regulation) almost always possess a homologue of the bacterial enzyme AlkB (e.g. ALKB2), and that such homologues are lost in organisms (or species) which do not have DNA methylation activity.

Interestingly, *P. aeruginosa* has lost A/kB relatively recently in evolution, and thus may be a particularly suitable target for the present therapeutic combination. As *P. aeruginosa* is a major health problem for subjects with chronic lung conditions (e.g. cystic fibrosis), the present therapeutic combination may be particularly suitable for treating infections in such patients. Thus, in one embodiment a therapeutic combination may be used for treating an infection with a pathogen in patient having a chronic lung condition, such as cystic fibrosis.

Similarly, *M. tuberculosis* lacks an A/kB homologue capable of alkylating (e.g. methylating) cytosine at the 3' position, such that a therapeutic combination of the present invention may be particularly suitable for treating tuberculosis (TB).

Any pathogen (e.g. infectious organism) lacking a gene for the control/reversal/tolerance of nucleic acid alkylation (e.g. monoalkylation) may be particularly vulnerable to a therapeutic combination of the invention. Thus, in one embodiment a pathogen (e.g. a bacterium, virus, protist, fungus and/or helminth) targeted with the present therapeutic combination may lack a gene selected from AlkA, A/kB, Ada, OGT, RecA, DinB, UmuCD, or a combination thereof. Suitably, the pathogen lacks an A/kB gene.

Thus, subjects having a pathogenic infection may be stratified based on whether a pathogen of the infection lacks one or more of said genes, and said subjects may be chosen as particularly suitable recipients of a therapeutic combination of the invention.

Reference to the *E. coli* genes AlkA, A/kB, Ada, OGT, RecA, DinB, UmuCD embraces a homologue thereof (e.g. a homologue present in a different domain, phylum, class, order, family or genus). The skilled person is aware of tools and techniques suitable for identifying and/or classifying homologous genes (see, for example, section 'Sequence Identity' below).

An exemplary A/kb sequence is provided in SEQ ID NO: 1 (which corresponds to NCBI Reference Sequence: NC_000913.3). An A/kb homologue may demonstrate at least 60%, at least 70%, at least 80%, or at least 90% sequence identity to the sequence of SEQ ID NO: 1. For example, an A/kb homologue may demonstrate at least 80%, or at least 90% sequence identity to the sequence of SEQ ID NO: 1. Suitably, an A/kb homologue may demonstrate at least 90% sequence identity to the sequence of SEQ ID NO: 1

In a preferable embodiment a pathogen (e.g. a bacterium, virus, protist, fungus and/or helminth) targeted with the present therapeutic combination may lack A/kB, or a homologue thereof.

In one embodiment, the pathogen (preferably pathogen lacking an AlkB homologue) is one or more metazoan selected from *Trichoplax adherens, Schistoma mansoni, Brugia malayi*, and *Ixodes scapularis*.

Non-pathogenic metazoan organisms to which a therapeutic combination of the invention may be applied include *Enoplus brevis, Caenorhabditis elegans, Hypsibium dujardini, Daphnia magna, Apis mellifera, Dendroctus ponderosae, Danaus plexippus* and *Drosophila melanogaster*.

In one embodiment, the pathogen (preferably a pathogen lacking an A/kB homologue) is one or more protist selected from *Entamoeba histolytica, Trichomonas vaginalis, Blastocystis hominis, Leishmania* Spp., and *Giardia lamblia*.

Non-pathogenic protist organisms to which a therapeutic combination of the invention may be applied include *Fonticula alba, Dictyostelium discoideum, Chlamydomonas reinhardtii, Crytomonas paramedium, Paulinella chromatophora, Nannochloropsis gaditana, Tetrahymena* Spp.

In one embodiment, the pathogen (preferably a pathogen lacking an A/kB homologue) is one or more fungi selected from *Encephalitozoan cuniculi, Nasema apis, Namema ceranae, Vittaforma carneae, Enterocytosoan bieneusi, Spraguea lophii, Vavra culiculis, Edharzardia aedes, Nematocida parisii, Razella* Spp., *Parasitella parasitica, Lichteimia ramose, Sporisorium scitamineum, Trametes versicolor*, and *Punctularia strigosozonata*.

In one embodiment, the pathogen (preferably a pathogen lacking an AlkB homologue) is one or more ascomycota selected from *Drechslera stenobrocha*, and *Candida albicans*, or a combination thereof.

Non-pathogenic ascomycota organisms to which a therapeutic combination of the invention may be applied include *Schizosacchardmyces pombe*, and *Saccharomyces cerevisiae*, or a combination thereof.

In one embodiment, the pathogen (preferably a pathogen lacking an AlkB homologue) is one or more Actinobacteria selected from *Mycobacterium tuberculosis* NCGM2209, *Mycobacterium leprae* TN, *Tropheiyma whipplei* TWO8/27, and *Mycobacterium ulcerans Agy*99, or a combination thereof.

In one embodiment, the pathogen (preferably a pathogen lacking an A/kB homologue) is one or more Alphaproteobacteria selected from *Rickettsia rickettsii* str. Hauke, *Ehrlichia canis* str. Jake, *Bartonella henselae* str. Houston-1, *Ehrlichia chaffeensis* str. Arkansas, and *Bartonella quintana* str. Toulouse, or a combination thereof.

In one embodiment, the pathogen (preferably a pathogen lacking an A/kB homologue) is one or more Bacilli selected from *Streptococcus pneumoniae* GA04375, *Streptococcus agalactiae* BSU247, *Staphylococcus aureus* subsp. *aureus* MSHR1132, *Staphylococcus epidermidis* NIH051668, *Listeria monocytogenes* FSL J2-071, *Enterococcus faecalis* ERV103, *Enterococcus faecium* TX0133C, *Listeria innocua* Clip11262, *Bacillus anthracis* str. A0442, *Bacillus cereus* Rock1-3, *Streptococcus pyogenes* MGAS315, and *Staphylococcus saprophyticus* subsp. *saprophyticus* ATCC 15305, or a combination thereof.

In one embodiment, the pathogen (preferably a pathogen lacking an AlkB homologue) is *Bacteroides fragilis* HMW 615.

In one embodiment, the pathogen (preferably a pathogen lacking an A/kB homologue) is one or more Betaproteobacteria selected from *Neisseria meningitidis* M04-240196, and *Neisseria gonorrhoeae* PID1, or a combination thereof.

In one embodiment, the pathogen (preferably a pathogen lacking an A/kB homologue) is one or more Chlamydiae selected from *Chlamydophila pneumoniae* J138, *Chlamydia trachomatis* F/SotonF3, and *Chlamydia psittaci* NJ1, or a combination thereof.

In one embodiment, the pathogen (preferably a pathogen lacking an AlkB homologue) is one or more Clostridia selected from *Clostridium botulinum* A str. ATCC 3502, *Clostridium difficile* NAP08, *Clostridium perfringens* str. 13, and *Clostridium tetani* E88, or a combination thereof.

In one embodiment, the pathogen (preferably a pathogen lacking an A/kB homologue) is one or more Gammaproteobacteria selected from *Acinetobacter baumannii* ATCC 17978, *Pseudomonas aeruginosa* LESB58, *Haemophilus influenzae* 22.4-21, *Francisella tularensis* subsp. *tularensis* SCHU S4, *Stenotrophomonas maltophilia* R551-3, *Yersinia pseudotuberculosis* IP 31758, *Yersinia pestis* biovar *Orientalis* str. BA200901799, *Legionella pneumophila* str. Lens, *Stenotrophomonas* sp. SKA14, and *Vibrio cholera* CIRS 101, or a combination thereof.

In one embodiment, the pathogen (preferably a pathogen lacking an A/kB homologue) is one or more Mollicutes selected from *Ureaplasma urealyticum* serovar 4 str. ATCC 27816, and *Mycoplasma pneumoniae* M129, or a combination thereof.

In one embodiment, the pathogen (preferably a pathogen lacking an A/kB homologue) is one or more Proteobacteria selected from *Campylobacter jejuni* subsp. *jejuni* LMG 23218, and *Helicobacter pylori* SouthAfrica7, or a combination thereof.

In one embodiment, the pathogen (preferably a pathogen lacking an A/kB homologue) is one or more Spirochaetia selected from *Treponema pallidum* subsp. *pallidum* str. Nichols, *Leptospira santarosai* str. 2000027870, *Borrelia burgdorferi* 29805, *Leptospira interrogans* serovar Copenhageni str. Fiocruz LV2791, *Leptospira weilii* serovar Topaz str. LT2116, *Leptospira noguchii* str. 2006001870, *Borrelia afzelii* PKo, *Borrelia recurrentis* A1, and *Borrelia garinii* PBr, or a combination thereof.

For the avoidance of doubt, a pathogen may comprise an A/kB homologue. Given the protective role of AlkB/an AlkB homologue (in the removal of alkylation damage from nucleic acid) and the alkylating (e.g. methylating) role of a DNMT enzyme (e.g. DNMT1 and/or DNMT2), a pathogen having a high level of DNMT expression relative to A/kB expression may be particularly sensitive to a therapeutic combination of the invention. The skilled person understands how to determine expression of genes, which may be achieved by way of e.g. microarray analysis, reverse transcriptase polymerase chain reaction (RT-PCT), northern blot, Serial analysis of gene expression (SAGE), Fluorescent in situ hybridization (FISH), and/or RNA-sequencing (RNA-seq).

Said gene expression may be absolute gene expression or relative gene expression. The determination of relative expression may comprise analysing expression of a DNMT gene and/or expression of A/kB homologue gene relative to the expression of a suitable standard/reference gene (e.g. a housekeeping gene).

In one embodiment, a pathogen comprises high ratio of DNMT gene expression to A/kB homologue gene expression. In one embodiment, the ratio of DNMT gene expression to A/kB homologue gene expression is one or more selected from about 2:1, about 5:1, about 10:1, about 15:1, about 20:1, about 25:1, about 30:1, about 35:1, about 40:1, about 45:1, and about 50:1.

Furthermore, many strains of bacteria (in particular of *M. tuberculosis*) have been reported to have resistance to certain aminoglycoside antibiotics (notably kanamycin), and thus the ability to purposefully use such antibiotics as part of the therapeutic combination (e.g. enhanced therapeutic combination) of the present invention makes such resistant strains particularly suitable targets.

An assessment of said "enhanced suppression of a pathogen", is demonstrated by reference to the accompanying Examples, and may be assessed using the methodology described in the Examples (e.g. Example 1). For example, Example 1 describes a method that measures the number of colony forming units (CFU) in a sample treated with the therapeutic combination with a sample that is not treated with one (or neither) of the constituent parts of the therapeutic combination. This allows for direct comparison of pathogen suppression between a therapeutic combination of the invention, and an otherwise identical composition lacking an aminoglycoside antibiotic or a nucleic acid monoalkylating agent (or both).

In one embodiment, suppression of a B-cell malignancy is considered to be enhanced when the "CFU" value obtained for a combination of the two principal active compounds (e.g. an aminoglycoside antibiotic, and a nucleic acid monoalkylating agent) is less that the "CFU" value obtained when either an aminoglycoside antibiotic of the invention, or a nucleic acid monoalkylating agent is absent (but under otherwise identical conditions).

Thus in one embodiment enhanced suppression of a pathogen may be determined by comparing the "CFU" value obtained for a combination of an aminoglycoside antibiotic of the invention, and a nucleic acid monoalkylating agent with the "CFU" value obtained for the same formulation/composition absent an aminoglycoside antibiotic of the invention, or a nucleic acid monoalkylating agent under the same conditions.

In one embodiment the present invention provides CFU value that is at least about 5%, 10%, 15%, 20%, 25%, 30%, 35%, 40%, 45%, 50%, 55%, 60%, 65%, 70%, 75%, 80%, 85%, 90% or 95% (preferably at least about 5%, 10%, 15%, 20%, 25%, 30%; more preferably at least about 10%) less than a CFU value provided by the same formulation (e.g. composition) absent an aminoglycoside antibiotic of the invention, or absent a nucleic acid monoalkylating agent, but otherwise under the same conditions.

In one embodiment a therapeutic combination of the invention may exhibit synergistic suppression of a pathogen.

The term "synergistic" as used herein means that the suppression of pathogen exhibited is greater than the sum of its parts. In other words, the suppression of a pathogen is more than additive.

Any cell (e.g. tumour) or organism in which a nucleic acid (e.g. DNA) may be alkylated may be targeted by a therapeutic combination of the invention. Thus, a therapeutic combination of the invention may advantageously be used to suppress tumours in a subject suffering from cancer.

In more detail, the present therapeutic combination may further be used to increase the efficacy of a chemotherapy which involves the administration of a nucleic acid monoalkylating agent. This is highly surprising, as aminoglycosides are not traditionally used as part of (e.g. as an adjuvant in) such cancer therapies.

Thus, in a further aspect, there is provided a therapeutic combination for use in treating cancer, said therapeutic combination comprising:
  a. an antibiotic; and
  b. a further nucleic acid monoalkylating agent that substitutes a single nucleotide of a nucleic acid with an alkyl group.

In another aspect, there is provided a therapeutic combination for use in treating cancer, said therapeutic combination comprising:
  a. an aminoglycoside antibiotic; and
  b. a further nucleic acid monoalkylating agent that substitutes a single nucleotide of a nucleic acid with an alkyl group.

In one embodiment, the therapeutic combination provides an enhanced suppression of a cancer (preferably of a cancer cell; more preferably of a tumour) when compared with an otherwise identical composition lacking said aminoglycoside antibiotic. In one embodiment, the therapeutic combination provides an enhanced suppression of a cancer (preferably of a cancer cell; more preferably of a tumour) when compared with an otherwise identical composition lacking said nucleic acid monoalkylating agent.

Suitably, said therapeutic combination may be administered to a subject. The subject may not have been previously diagnosed as having cancer. Alternatively, the subject may have been previously diagnosed as having cancer. The subject may also be one who exhibits disease risk factors, or one who is asymptomatic for cancer. The subject may also be one who is suffering from or is at risk of developing cancer. In one embodiment, the subject has been previously administered a therapy for cancer.

In embodiments in which the method of therapy is a method of treating cancer, a dosage of the therapeutic combination may be chosen which maximises damage of cancer cells and minimises damage of non-cancer cells.

In one embodiment, said cancer is one or more selected from glioblastoma (e.g. glioblastoma multiforme), Acute Myeloid Leukemia, breast cancer, leukemia, lymphoma, Hodgkin's disease, multiple myeloma, sarcoma, lung cancer (small and/or non-small cell lung cancer), ovarian cancers, astrocytoma, bone sarcoma, non-Hodgkin lymphoma, chronic lymphocytic leukaemia, myeloma, Waldenstrom's macroglobulinaemia, small cell lung cancer, neuroblastoma, testicular cancer, soft tissue sarcoma, osteosarcoma, bladder cancer, small cell lung cancer, cervical cancer, pancreatic cancer, a neuroendocrine tumour, polycythemia vera, myeloid metaplasia, fibrosarcomas, rhabdomyosarcoma, islet cell carcinoma, medullary thyroid cancer, anaplastic astrocytoma, head and neck cancer, esophageal cancer, stomach cancer, prostate cancer, mesothelioma, and endometrial cancer.

In a preferable embodiment, said cancer may be one or more selected from Glioblastoma, Acute Myeloid Leukemia and breast cancer.

Suitably, said breast cancer may be BRCA deficient (e.g. BRCA1 and/or BRCA2 deficient).

Interestingly, DNMT activity is important in the pathogenesis of Acute Myeloid Leukemia (AML), such that AML may be a particularly suitable target of a therapeutic combination of the invention. Thus, in one embodiment said cancer is Acute Myeloid Leukemia.

A cancer cell (e.g. tumor) of said cancer may comprise an expression level of a DNMT that is higher than an expression level of DNMT in a reference standard, wherein the reference standard is from a healthy cell. Preferably, a healthy cell is a non-cancer cell.

A cancer cell (e.g. tumor) of said cancer may comprise an expression level of alkB that is higher than an expression level of a/kb in a reference standard, wherein the reference standard is from a healthy cell. Preferably, a healthy cell is a non-cancer cell.

A cancer may be stratified by the ratio of DNMT gene expression to A/kB homologue gene expression. For example, a cancer cell of the cancer may have a high level of DNMT gene expression relative to the level of AlkB homologue gene expression.

In one embodiment, a cancer cell comprises a high ratio of DNMT gene expression to AlkB homologue gene expression. In one embodiment, the ratio of DNMT gene expression to AlkB homologue gene expression is one or more selected from about 2:1, about 5:1, about 10:1, about 15:1, about 20:1, about 25:1, about 30:1, about 35:1, about 40:1, about 45:1, and about 50:1.

In one embodiment, a cancer cell has a decreased expression of an AlkB homologue gene relative to the expression of an AlkB homologue gene in a non-cancer cell (e.g. a healthy cell). In one embodiment, a cancer cell has an increased expression of a DNMT gene relative to the expression of a DNMT gene in a non-cancer cell (e.g. a healthy cell). In one embodiment, a cancer cell has a decreased expression of AlkB homologue gene relative to the expression of an AlkB homologue gene in a non-cancer cell and an increased expression of a DNMT gene relative to the expression of a DNMT gene in a non-cancer cell.

In one embodiment, said AlkB homologue is one or more selected from AlkB homolog 1, histone h2a dioxygenase, ALKBH2, ALKBH3, ALKBH4, ALKBH5, ALKBH6, ALKBH7, ALKBH8, and FTO, or a combination thereof. In a suitable embodiment, said AlkB homologue is ALKBH2.

In one embodiment, said DNMT is one or more selected from DNMT1, DNMT3A, and DNMT3B.

Suitably, said non-cancer cell is a cell from the same organ and/or tissue in which the cancer (e.g. tumour of the cancer) is present.

In one aspect, there is provided a kit for use in a method of treating cancer comprising:
a. an antibiotic; and
b. a further nucleic monoalkylating agent that substitutes a single nucleotide of a nucleic acid with an alkyl group.

In one aspect, there is provided a kit for use in a method of treating cancer comprising:
a. an aminoglycoside antibiotic; and
b. a further nucleic acid monoalkylating agent that substitutes a single nucleotide of a nucleic acid with an alkyl group.

Said kit may further comprise a housing for containing the antibiotic (e.g. aminoglycoside antibiotic) and the monoalkylating agent.

In one embodiment, an antibiotic and a monoalkylating agent are comprised within the same composition. In another embodiment, an antibiotic and a monoalkylating agent are comprised within separate compositions. In one embodiment, an aminoglycoside antibiotic and a monoalkylating agent are comprised within the same composition. In another embodiment, an aminoglycoside antibiotic and a monoalkylating agent are comprised within separate compositions.

In one embodiment, a kit may comprise instructions to use the kit in a method for treating cancer. Said instructions may include, for example, the optimal dose of a therapeutic combination to be administered, the optimal time(s) to administer a therapeutic combination, the optimal administration method(s), or any other information relevant to using a therapeutic combination to treat cancer.

Said instructions may be provided as part of a label, or as part of an instruction manual provided either together with or separately to the kit.

The following embodiments and definitions may pertain to any aspect (or other embodiment) of the invention described herein e.g. to any method, use, composition, therapeutic combination, therapeutic combination for use, agent combination for use, kit, or kit for use described herein.

In one embodiment, a therapeutic combination of the invention may be administered by one or more selected from oral, intravenous, intramuscular, subcutaneous, and intradermal administration, or a combination thereof. An antibiotic (e.g. aminoglycoside antibiotic) and a nucleic acid monoalkylating agent may be administered by the same or by separate means. For example, an antibiotic (aminoglycoside antibiotic) may be administered orally, and a nucleic acid monoalkylating agent may be administered intravenously.

The aminoglycoside class of antibiotics consists of about ten different antibiotics, each having common mechanisms of action. The aminoglycosides primarily act by binding to the aminoacyl site of 16S ribosomal RNA within the 30S ribosomal subunit, which leads to misreading of the genetic code and thus inhibition of translocation. The initial steps required for peptide synthesis, such as binding of mRNA and the association of the 50S ribosomal subunit, are uninterrupted, but elongation fails to occur due to disruption of the mechanisms for ensuring translational accuracy. The resulting antimicrobial activity is typically bactericidal against susceptible aerobic gram-negative bacilli. The most common clinical application of the aminoglycosides is for the treatment of serious infections caused by aerobic gram-negative bacilli.

In one embodiment, an aminoglycoside is one or more selected from kanamycin (e.g. kanamycin A), amikacin, tobramycin, dibekacin, gentamicin, sisomicin, netilmicin, neomycin, streptomycin, or a combination thereof. Such antibiotics are often used/administered in salt form, and as such any salt of an aminoglycoside antibiotic is encompassed by the invention.

In one embodiment, an aminoglycoside is one or more selected from kanamycin (e.g. kanamycin A), amikacin, tobramycin, dibekacin, sisomicin, netilmicin, neomycin, streptomycin, or a combination thereof.

Said neomycin may be one or more of neomycin B, neomycin C, or neomycin E (e.g. paromomycin).

In a preferable embodiment, an aminoglycoside antibiotic is one or more selected from kanamycin (e.g. kanamycin A) and neomycin. Suitably, said aminoglycoside antibiotic is kanamycin (e.g. kanamycin A).

In one embodiment, a penicillin antibiotic is one or more selected from benzylpenicillin (penicillin G), procaine benzylpenicillin (procaine penicillin), benzathine benzylpenicillin (benzathine penicillin), and phenoxymethylpenicillin (penicillin V), or a combination thereof.

In one embodiment, a cephalosporin antibiotic is one or more selected from cefazolin, cefaclor, cefdinir, ceftin, cefuroxime, cefadroxil, cephalexin, cefepime, ceftriaxone, cefixime, and ceftaroline fosamil, or a combination thereof.

In one embodiment, a macrolide antibiotic is one or more selected from azithromycin, clarithromycin, erythromycin, fidaxomicin, and telithromycin, or a combination thereof.

In one embodiment, a fluoroquinolone antibiotic is one or more selected from ciprofloxacin, delafloxacin, gemifloxacin, levofloxacin, moxifloxacin, norfloxacin, and ofloxacin, or a combination thereof.

In one embodiment, a sulphonamide antibiotic is one or more selected from sulfacetamide, sulfadiazine, sulfadimidine, sulfafurazole (sulfisoxazole), sulfisomidine, sulfamethoxazole, sulfamoxole, sulfanitran, sulfadimethoxine, sulfamethoxypyridazine, sulfametoxydiazine, sulfadoxine, sulfametopyrazine, and terephtyl, and a combination thereof.

In one embodiment, a tetracycline antibiotic is one or more selected from tetracycline, chlortetracycline, oxytetracycline, demeclocycline, lymecycline, meclocycline, methacycline, minocycline, rolitetracycline, tigecycline, and doxycycline, or a combination thereof.

In one embodiment a nucleic acid monoalkylating agent is one or more selected from N-methyl-N'-nitro-N-nitrosoguanidine (MNNG), methyl methanesulfonate (MMS), dacarbazine, methylnitrosourea (MMU), ethyl methanesulfonate (EMS), temozolomide (TMZ), ethylnitrosourea (ENU), diethyl nitrosamine (DEN), and N-Nitroso-N-methylurea (NMU).

In one embodiment a nucleic monoalkylating agent is one or more selected from dacarbazine, methylnitrosourea (MMU), ethyl methanesulfonate (EMS), temozolomide (TMZ), ethylnitrosourea (ENU), diethyl nitrosamine (DEN), and N-Nitroso-N-methylurea (NMU)

In a preferable embodiment, said alkylating agent is temozolomide (TMZ).

Methyl methanesulfonate (PubChem CID: 4156) typically methylates DNA on N7-deoxyguanosine and N3-deoxyadenosine, and may also methylate at other oxygen and nitrogen atoms in DNA bases, and may also methylate the phosphodiester linkage of a nucleic acid.

Methyl methanesulfonate (MMS) may have the following structure:

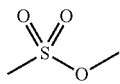

Ethyl methanesulfonate (PubChem CID: 6113) may have the following structure:

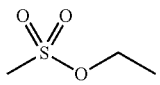

Temozolomide (PubChem CID: 5394) may have the following structure:

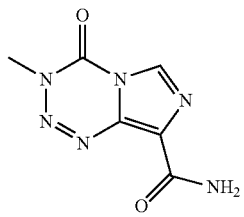

Ethylnitrosourea (PubChem CID: 12967) may have the following structure:

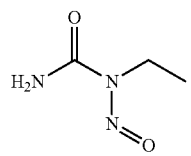

N-Nitroso-N-methylurea (NMU) (PubChem CID: 12699) may have the following structure:

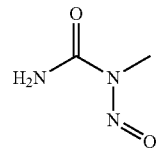

N-methyl-N'-nitro-N-nitrosoguanidine (PubChem CID: 6261) may have the following structure:

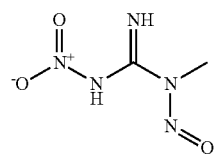

Dacarbazine (PubChem CID: 2942) may have the following structure:

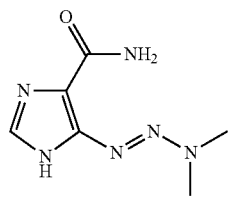

Diethyl nitrosamine (PubChem CID: 5921) may have the following structure:

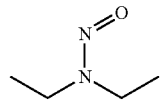

Such nucleic acid monoalkylating agents typically result in a nucleic acid (e.g. a base/nucleotide of a nucleic acid) becoming substituted with an alkyl when said nucleic acid is contacted with said monoalkylating agent.

An "Alkyl" (synonymous with the term "alkyl group" and "alkyl substituent") may be a saturated or unsaturated, straight or branched, hydrocarbon chain. An alkyl group have 1-18 carbon atoms, e.g. an alkyl group may be a C1-C18 group, or is a C1-012 group, a C1-C6 group, or a C1-C4 group. A lower alkyl group may typically have 1-6 carbons (and may be chain may be straight or branched). An alkyl group may have zero branches (e.g. is a straight chain), one branch, two branches, or more than two branches. In one embodiment, an alkyl group may be saturated. In another embodiment, an alkyl group may be unsaturated. In one embodiment, an unsaturated alkyl may have one double bond, two double bonds, more than two double bonds, and/or one triple bond, two triple bonds, or more than two triple bonds. Alkyl chains may be optionally substituted with 1 substituent (e.g. the alkyl group is mono-substituted), or 1-2 substituents, or 1-3 substituents, or 1-4 substituents, etc. The substituents may be one or more selected from the group consisting of hydroxy, amino, alkylamino, boronyl, carboxy, nitro, cyano, or a combination thereof. An alkyl group incorporating one or more heteroatoms may be referred to as a heteroalkyl group.

In one embodiment, an alkyl group may be one or more selected from methyl, ethyl, n-propyl, isopropyl, n-butyl, t-butyl, n-pentyl, heptyl, nonyl, decyl, or a combination thereof. Suitably, an alkyl group may be one or more selected from methyl, ethyl, or a combination thereof (preferably methyl).

In one embodiment, an alkylating agent is one or more selected from methyl methanesulfonate (MMS), MMU, ethyl methanesulfonate (EMS), temozolomide (TMZ), ethylnitrosourea (ENU), and methylnitrosourea (NMU).

Many of such nucleic acid monoalkylating agents have been previously been used only as part of a chemotherapy. Thus, the present invention provides and advantageous further application for such agents, namely for the suppression of bacteria.

In one embodiment, a nucleic acid monoalkylating agent may be a nitrosourea. Suitably, a nitrosourea may be one or more selected from MMU, ENU, NMU, or a combination thereof.

In one embodiment, said nucleic acid monoalkylating agent is MNNG, and said aminoglycoside antibiotic is one or more selected from kanamycin, amikacin, tobramycin, dibekacin, gentamicin, sisomicin, netilmicin, neomycin, and streptomycin, or a salt thereof.

In one embodiment, said nucleic acid monoalkylating agent is MMS, and said aminoglycoside antibiotic is one or more selected from kanamycin, amikacin, tobramycin, dibekacin, gentamicin, sisomicin, netilmicin, neomycin, and streptomycin, or a salt thereof.

In one embodiment, said nucleic acid monoalkylating agent is dacarbazine, and said aminoglycoside antibiotic is one or more selected from kanamycin, amikacin, tobramycin, dibekacin, gentamicin, sisomicin, netilmicin, neomycin, and streptomycin, or a salt thereof.

In one embodiment, said nucleic acid monoalkylating agent is MMU, and said aminoglycoside antibiotic is one or more selected from kanamycin, amikacin, tobramycin, dibekacin, gentamicin, sisomicin, netilmicin, neomycin, and streptomycin, or a salt thereof.

In one embodiment, said nucleic acid monoalkylating agent is EMS, and said aminoglycoside antibiotic is one or more selected from kanamycin, amikacin, tobramycin, dibekacin, gentamicin, sisomicin, netilmicin, neomycin, and streptomycin, or a salt thereof.

In one embodiment, said nucleic acid monoalkylating agent is TMZ, and said aminoglycoside antibiotic is one or more selected from kanamycin, amikacin, tobramycin, dibekacin, gentamicin, sisomicin, netilmicin, neomycin, and streptomycin, or a salt thereof.

In one embodiment, said nucleic acid monoalkylating agent is ENU, and said aminoglycoside antibiotic is one or more selected from kanamycin, amikacin, tobramycin, dibekacin, gentamicin, sisomicin, netilmicin, neomycin, and streptomycin, or a salt thereof.

In one embodiment, said nucleic acid monoalkylating agent is DEN, and said aminoglycoside antibiotic is one or more selected from kanamycin, amikacin, tobramycin, dibekacin, gentamicin, sisomicin, netilmicin, neomycin, and streptomycin, or a salt thereof.

In one embodiment, said nucleic acid monoalkylating agent is NMU, and said aminoglycoside antibiotic is one or more selected from kanamycin, amikacin, tobramycin, dibekacin, gentamicin, sisomicin, netilmicin, neomycin, and streptomycin, or a salt thereof.

In a preferable embodiment, a nucleic acid monoalkylating agent of the invention is a DNA monoalkylating agent. Such a nucleic acid/DNA monalkylating agent is not limited to a monoalkylating agent that alkylates only a nucleic acid (or e.g. only DNA). For example, the monoalkylating agent may be capable of alkylating an alternative molecule, such as a polypeptide.

Suitably, an aminoglycoside antibiotic synergises with a nucleic acid monoalkylating agent to result in an increase in the amount of nucleic acid alkylation (e.g. toxic DNA alkylation) which occurs in a cell (e.g. bacterial cell) or organism to which a combination of such agents is applied. Thus, an aminoglycoside antibiotic may enhance alkylation of a nucleic acid in the presence of a monoalkylating agent. In a further embodiment, an aminoglycoside enhances the nucleic acid alkylating activity of a nucleic acid monoalkylating agent to increase nucleic acid (e.g. nucleotide) alkylation. Preferably, said nucleic acid alkylation is toxic DNA alkylation.

In one embodiment, a nucleic acid monoalkylating agent substitutes a nucleotide of a nucleic acid with an alkyl group to provide one or more nucleotide adduct, preferably a one or more nucleotide adduct selected from 3-methylcytosine (3meC), 3-methylguanine (3meG), 3-methyladenine (3meA), 8-oxoguanine (8-oxo-G), $O^2$-alkylthymine, $O^4$-alkylthymine, $O^6$-methylguanine, $O^6$-ethylguanine, or any combination thereof.

In one embodiment, a nucleic acid monoalkylating agent substitutes a nucleotide (e.g. of a nucleic acid) with an alkyl group to provide one or more nucleotide adduct selected from 3-methylcytosine (3meC), 3-methylguanine (3meG), 3-methyladenine (3meA), $O^2$-alkylthymine, $O^4$-alkylthymine, $O^6$-methylguanine, $O^6$-ethylguanine, or any combination thereof.

In one embodiment a nucleic acid monoalkylating agent substitutes (e.g. methylates) cytosine with a methyl group at the number 3 position (e.g. at the number 3 nitrogen) to provide the nucleotide adduct 3meC.

In one embodiment, a nucleic acid monoalkylating agent substitutes (e.g. methylates) guanine at the number 3 position (e.g. at the number 3 nitrogen) with an alkyl group to provide the nucleotide adduct 3meG.

In one embodiment, a nucleic acid monoalkylating agent substitutes (e.g. methylates) adenine at the number 3 position (e.g. at the number 3 nitrogen) with an alkyl group to provide 3meA.

In one embodiment, a nucleic acid monoalkylating agent substitutes (e.g. alkylates) thymine at the O2 position with an alkyl group to provide $O^2$-alkylthymine.

In one embodiment, a nucleic acid monoalkylating agent substitutes (e.g. alkylates) thymine at the O4 position with an alkyl group to provide the nucleotide adduct $O^4$-alkylthymine.

In one embodiment, a nucleic acid monoalkylating agent substitutes (e.g. alkylates) thymine at the O6 position with an alkyl group to provide the nucleotide adduct $O^6$-alkylthymine.

In one embodiment, a nucleic acid monoalkylating agent substitutes (e.g. methylates) guanine at the O6 position with an alkyl group to provide the nucleotide adduct $O^6$-methylguanine.

In one embodiment, a nucleic acid monoalkylating agent substitutes (e.g. methylates) guanine at the O6 position with an alkyl group to provide the nucleotide adduct $O^6$-ethylguanine.

In one embodiment, a nucleic acid monoalkylating agent substitutes a nucleotide or a nucleic acid to provide one or more nucleotide adduct selected from 3meC, 3meG, 3meA, 8-oxo-G, $O^2$-alkylthymine, $O^4$-alkylthymine, $O^6$-methylguanine, and $O^6$-ethylguanine.

Any combination of antibiotics/aminoglycoside antibiotics(s) and nucleic acid monoalkylating agent(s) is encompassed by the invention. For example, a therapeutic combination or composition may comprise a plurality of aminoglycoside(s) and/or a plurality of nucleic acid monoalkylating agent(s). Different combinations may be chosen based on the disease/pathogen/infection to be treated, and different combinations may be optimal for a particular disease. Given the broad array of antibiotics/aminoglycoside antibiotics and nucleic acid monoalkylating agents encompassed within a therapeutic combination/composition of the invention, this allows for enhanced treatment of a multitude of infections, and furthermore a multitude of infections within this class (e.g. bacterial, viral, fungal etc. infection) which are caused by a multitude of different pathogens.

In one embodiment, a therapeutic combination may comprise at least two, three, four, five, six, seven, eight, nine or ten aminoglycoside antibiotics. For example, a therapeutic combination may comprise at least two, three, four or five aminoglycoside antibiotics.

In one embodiment, a therapeutic combination may comprise at two, three, four, five, six, seven, eight, nine or ten nucleic acid monoalkylating agents. For example, a therapeutic combination may comprise at least two, three, four or five nucleic acid monoalkylating agents.

Sequence Identity

Reference to a gene or polypeptide described herein embraces a homologue thereof. The skilled person also understands how to employ appropriate sequence alignment to identify homologous/analogous nucleic acid/polypeptide sequences.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics: 1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

| ALIGNMENT SCORES FOR DETERMINING SEQUENCE IDENTITY | | | | | | | | | | | | | | | | | | | |
|---|---|---|---|---|---|---|---|---|---|---|---|---|---|---|---|---|---|---|---|
|  | A | R | N | D | C | Q | E | G | H | I | L | K | M | F | P | S | T | W | Y | V |
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |

-continued

ALIGNMENT SCORES FOR DETERMINING SEQUENCE IDENTITY

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of identical matches}}{[\text{length of the longer sequence plus the number of gaps introduced into the longer sequence in order to align the two sequences}]} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an alkylating agent" includes a plurality of such agents and reference to "the aminoglycoside antibiotic" includes reference to one or more aminoglycoside antibiotics and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

Embodiments of the invention will now be described, by way of example only, with reference to the following Figures and Examples.

EXAMPLES

Materials & Methods

Overexpression of mSSSI in E. coli

The mSSSI-expressing plasmid pAIT2, containing a Kanamycin resistance gene (encoding neomycin phosphotransferase II), was a gift from New England Biolabs. It expresses the mSSSI methyltransferase (a DNMT) under the control of the IPTG-inducible pTac promoter.

Standard CaCl$_2$) transformation was used to introduce the pAIT2 plasmid into the E. coli strain C2353 (NEB), either without (WT) or with (ALKB) deletion of the alkB gene. Basal activity of the mSSSI gene in both backgrounds was verified by using a methyl-sensitive restriction digest using HpaII and MspI.

To test the effect of alkylation damage on kanamycin resistance in the absence of DNMT overexpression a standard protein expression plasmid pET28a, which also carries the kanamycin resistance gene, was used as a negative control. Transformation into C2353 was as for pAIT2.

Example 1—Alkylating-Agent Sensitivity Assay Shows Aminoglycoside Synergy with an Alkylating Agent at Suppressing Bacterial Growth The synergy between exemplary aminoglycoside kanamycin and exemplary alkylating agent MMS is demonstrated.

E. coli strains were grown from single colonies in Luria Bertani (LB) media at 37° C. until they reached an OD of 0.6. The bacteria were then separated into different aliquots for different treatments, centrifuged at 3000 revolutions per minute (rpm) for 5 minutes to pellet down. Bacteria were then resuspended in LB media either with or without supplementation with 20 mM Methyl-methane-sulphate (MMS; Sigma-Aldrich) with or without Kanamycin at 50 ug/ml. After 30 minutes at 37° C., bacteria were washed extensively in LB to remove MMS and were plated on LB with or without Kanamycin at 50 ug/ml. Sensitivity was assayed by calculating the number of colony forming units (CFU) and taking the logarithm to base 10. The experiment was repeated three times for each condition and the mean and standard deviation plotted. Significance was calculated using a two-tailed t-test.

Figure 1:
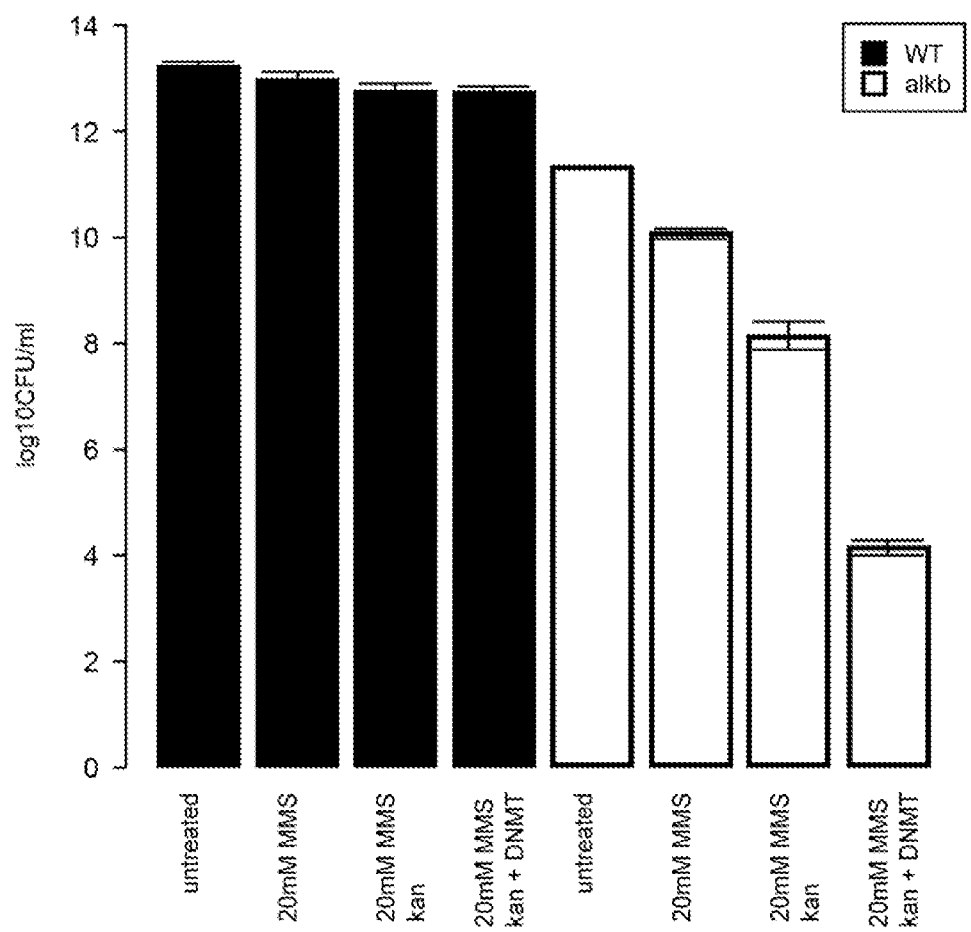
FIG. 1 demonstrates the synergistic effect of an alkylating agent and aminoglycoside antibiotic combination at suppressing bacteria. Error bars represent standard deviation from at least 3 repeats. CFU=colony forming units. The four bars on the left correspond to wild-type (WT) cells. The four bars on the right correspond to alkb−/− cells (alkb).
Figure 2:
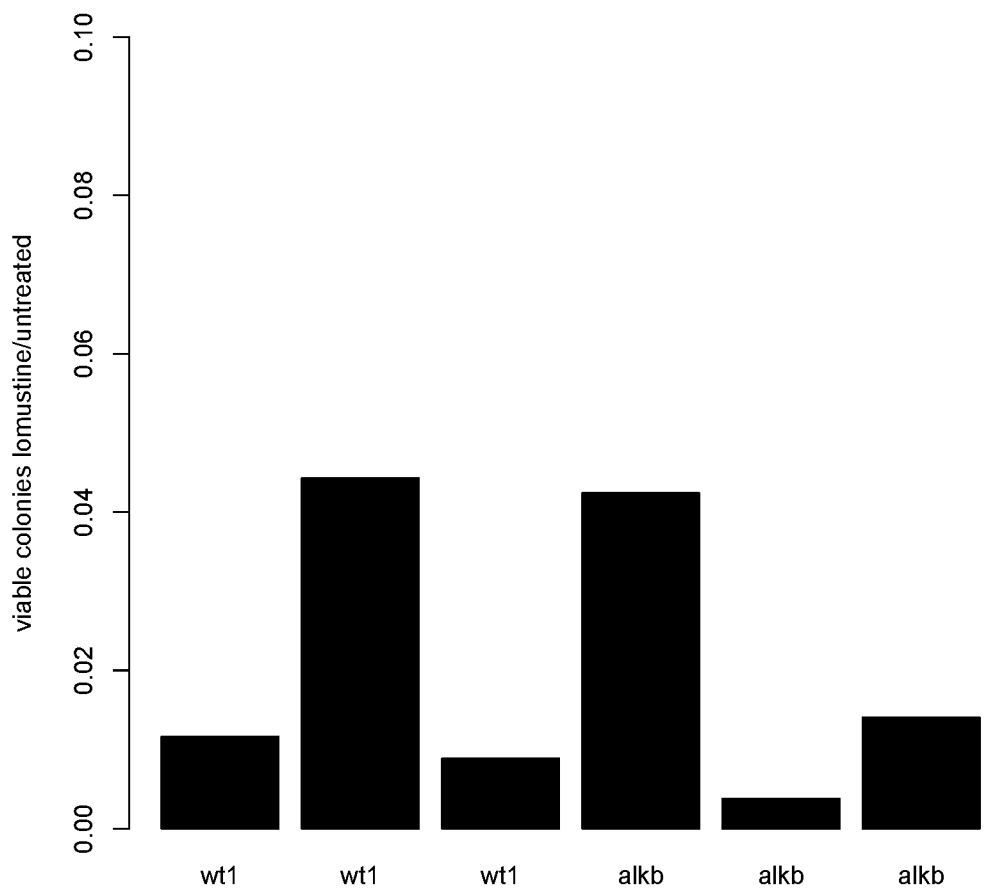
FIG. 2 demonstrates that there is no difference in sensitivity between WT and alkB mutants to the bifunctional alkylating agent lomustine in combination with kanamycin. wt=wildtype; alkb=alkb mutants (non-functional alkb). "viable colonies lomustine/untreated"=the ratio of colonies observed after lomustine treatment to those after DMSO treatment.
Figure 3:
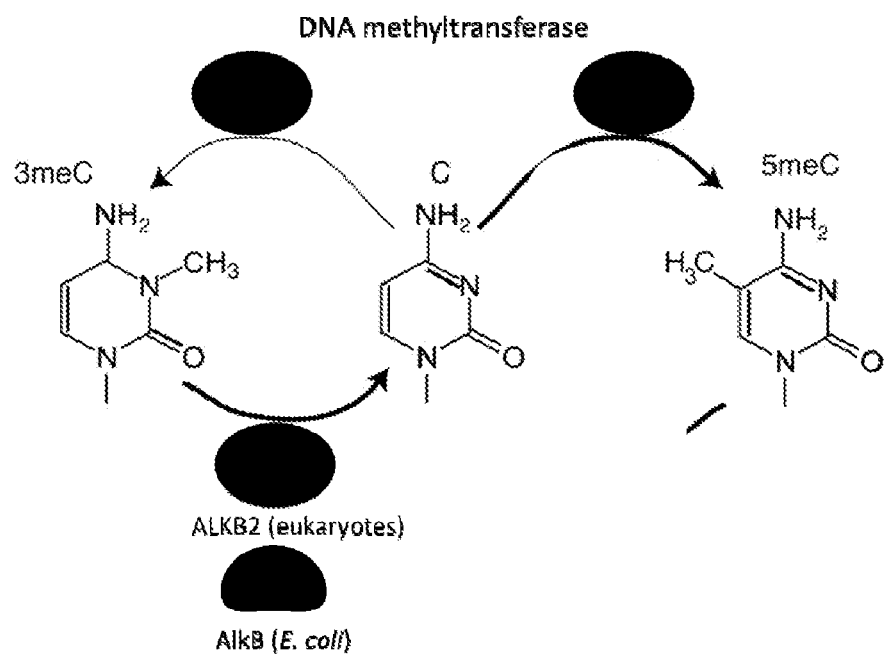
FIG. 3 provides a schematic demonstrating a model for the introduction of alkylation damage by DNA methyltransferase activity. The predominant activity is introduction of 5meC (thick arrow), but 3meC is also introduced as a low abundance by-product (thin arrow). 3meC is removed by the activity of ALKB2 in eukaryotes-ALKB2 is homologous to bacterial AlkB.

As shown in FIG. 1, a low dose of MMS at 20 mM is well tolerated by WT E. coli, having minimal effect on bacterial growth. Sensitivity to MMS was increased upon co-treatment with kanamycin, and even more so in bacteria expressing a DNMT. Surprisingly, this sensitivity was significantly increased in a/kB mutants, as was the synergy between MMS and kanamycin even though these bacteria possessed a plasmid encoding kanamycin resistance. This sensitivity and synergy was increased further still upon overexpression of a DNMT (an enzyme which can introduces toxic alkylation damage to DNA, see FIG. 2), suggesting that kanamycin synergises with MMS to increase the introduction of toxic 3meC alkylation damage to DNA.

Example 2—No Difference in Sensitivity Between WT and a/kB Mutants to the Bifunctional Alkylating Agent Lomustine in Combination with Kanamycin This experiment was carried out in a similar manner to that of Example 1, except lomustine was used instead of MMS.

Cells were grown in LB+50 ug/ml Kanamycin to an OD of 0.8 and treated for 2 hours with lomustine at 20 mM (in a similar manner as per Example 1) or DMSO (control). Cells expressed a kanamycin resistance gene (encoding neomycin phosphotransferase II).

Survival was measured as the number of colonies relative to the untreated control (DMSO control). The results are shown FIG. 2. Each bar is a biological replicate; the p-value from a two-tailed T-test was 0.93. No excess sensitivity of AlkB to lomustine+kanamycin combination was seen.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

```
SEQUENCES
(E. coli str, K-12 alkb; NCBI Reference Sequence:
NC_000913.3)
                                               SEQ ID NO: 1
ATGTTGGATCTGTTTGCCGATGCTGAACCGTGGCAAGAGCCACTGGCGGC

TGGTGCGGTAATTTTACGGCGTTTTGCTTTTAACGCTGCGGAGCAACTGA

TCCGCGATATTAATGACGTTGCCAGCCAGTCGCCGTTTCGCCAGATGGTC

ACCCCCGGGGATATACCATGTCGGTGGCGATGACCAACTGTGGGCATCT

GGGCTGGACGACCCATCGGCAAGGTTATCTCTATTCGCCCATTGATCCGC

AAACAAATAAACCGTGGCCCGCCATGCCACAGAGTTTTCATAATTTATGT

CAACGTGCGGCTACGGCGGCGGGCTATCCAGATTTCCAGCCAGATGCTTG

TCTTATCAACCGCTACGCTCCTGGCGCGAAACTGTCGCTGCATCAGGATA

AAGACGAACCGGATCTGCGCGCGCCAATTGTTTCTGTTTCTCTGGGCTTA

CCCGCGATTTTTCAATTTGGCGGCCTGAAACGAAATGATCCGCTCAAACG

TTTGTTGTTGGAACATGGCGATGTGGTGGTATGGGGCGGTGAATCGCGGC
```

-continued

```
TGTTTTATCACGGTATTCAACCGTTGAAAGCGGGGTTTCATCCACTCACC

ATCGACTGCCGCTACAACCTGACATTCCGTCAGGCAGGTAAAAAGAATA

A
``` and wherein said alkylated nucleotide adduct is one or more selected from 3meC, 3meG, 3meA, 8-oxo-G, O2-alkylthymine, O4-alkylthymine, O6-methylguanine, and O6-ethylguanine.

6. The method according to claim 1, wherein said pathogen lacks one or more gene encoding a polypeptide that removes an alkyl group from an alkylated nucleotide adduct;

The invention claimed is:

1. A method of suppressing, reducing or removing an infection with a pathogen in a subject, said method comprising administering a therapeutic combination to the subject, wherein said therapeutic combination comprises:
   a. an aminoglycoside antibiotic; and
   b. a nucleic acid monoalkylating agent that substitutes a single nucleotide of a nucleic acid with an alkyl group;
      wherein the therapeutic combination provides an enhanced suppression of a pathogen when compared with an otherwise identical composition lacking said aminoglycoside antibiotic; or
      wherein the therapeutic combination provides an enhanced suppression of a pathogen when compared with an otherwise identical composition lacking said nucleic acid monoalkylating agent.

2. The method according to claim 1, wherein said aminoglycoside antibiotic is administered prior to, simultaneously with or sequentially to said nucleic acid monoalkylating agent.

3. The method according to claim 1, wherein said pathogen is a bacterium.

4. The method according to claim 1, wherein said pathogen lacks one or more gene encoding a polypeptide that removes an alkyl group from an alkylated nucleotide adduct.

5. The method according to claim 1, wherein said pathogen lacks one or more gene encoding a polypeptide that removes an alkyl group from an alkylated nucleotide adduct; and wherein said gene is one or more selected from alkA and alkB.

7. The method according to claim 1, wherein said pathogen lacks one or more gene encoding a polypeptide that promotes tolerance of a cell to the presence of an alkylated nucleotide adduct within a nucleic acid of the cell.

8. The method according to claim 1, wherein said pathogen lacks one or more gene encoding a polypeptide that promotes tolerance of a cell to the presence of an alkylated nucleotide adduct within a nucleic acid of the cell; and wherein said one or more gene is selected from Ada, OGT, RecA, DinB, and UmuCD.

9. The method according to claim 1, wherein said pathogen is one or more selected from a *Salmonella* bacterium, a *Pseudomonas* bacterium, and a *Mycobacterium* bacterium.

10. The method according to claim 1, wherein said aminoglycoside antibiotic is one or more selected from kanamycin, amikacin, tobramycin, dibekacin, gentamicin, sisomicin, netilmicin, neomycin, and streptomycin, or a salt thereof.

11. The method according to claim 1, wherein said aminoglycoside antibiotic is kanamycin.

12. The method according to claim 1, wherein said nucleic acid monoalkylating agent is one or more selected from N-methyl-N'-nitro-N-nitrosoguanidine (MNNG), methyl methanesulfonate (MMS), dacarbazine, methylnitrosourea (MMU), ethyl methanesulfonate (EMS), temozolomide (TMZ), ethylnitrosourea (ENU), diethyl nitrosamine (DEN), and N-Nitroso-N-methylurea (NMU).

13. The method according to claim 1, wherein said nucleic acid monoalkylating agent is methyl methanesulfonate (MMS).

14. The method according to claim 1, wherein said nucleic acid monoalkylating agent substitutes a nucleotide of a nucleic acid with an alkyl group to provide one or more alkylated nucleotide adduct selected from 3meC, 3meG, 3meA, 8-oxo-G, O2-alkylthymine, O4-alkylthymine, O6-methylguanine, and O6-ethylguanine.

15. A method of in vitro disinfection, the method comprising applying an agent combination at a site comprising a pathogen, a site suspected of comprising a pathogen, or at a site at risk of comprising a pathogen, wherein said agent combination comprises:
   a. an aminoglycoside antibiotic; and
   b. a nucleic acid monoalkylating agent that substitutes a single nucleotide of a nucleic acid with an alkyl group;
   wherein the agent combination provides an enhanced suppression of a pathogen when compared with an otherwise identical composition lacking said aminoglycoside antibiotic; or
   wherein the agent combination provides an enhanced suppression of a pathogen when compared with an otherwise identical composition lacking said nucleic acid monoalkylating agent.

16. The method according to claim 15, wherein said applying comprises providing a local concentration of said aminoglycoside antibiotic and said nucleic acid monoalkylating agent at said site of about 1 mM to about 200 mM.

17. The method according to claim 1, wherein said pathogen lacks one or more gene encoding a polypeptide that removes an alkyl group from an alkylated nucleotide adduct; and wherein said gene is alkB.

18. The method according to claim 1, wherein said pathogen lacks one or more gene encoding a polypeptide that promotes tolerance of a cell to the presence of an alkylated nucleotide adduct within a nucleic acid of the cell; and wherein said alkylated nucleotide adduct is one or more selected from 3meC, 3meG, 3meA, 8-oxo-G, O2-alkylthymine, O4-alkylthymine, O6-methylguanine, and O6-ethylguanine.

19. The method according to claim 15, wherein said applying comprises providing:
   a. a local concentration of said aminoglycoside antibiotic of about 80 mM to about 120 mM; and/or
   b. a local concentration of said nucleic acid monoalkylating agent of about 1 mM to about 40 mM.

* * * * *